US008460297B2

(12) United States Patent
Watlington et al.

(10) Patent No.: US 8,460,297 B2
(45) Date of Patent: Jun. 11, 2013

(54) DRILL BIT ASSEMBLY FOR BONE TISSUE INCLUDING DEPTH LIMITING FEATURE

(75) Inventors: Michael B. Watlington, Plantation, FL (US); T. Tait Robb, Stewart, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 1563 days.

(21) Appl. No.: 12/001,863

(22) Filed: Dec. 13, 2007

(65) Prior Publication Data

US 2008/0167653 A1  Jul. 10, 2008

Related U.S. Application Data

(60) Provisional application No. 61/878,764, filed on Jan. 5, 2007.

(51) Int. Cl.
*A61B 17/56* (2006.01)

(52) U.S. Cl.
USPC ............................................................ 606/80

(58) Field of Classification Search
USPC ............. 606/72–75, 79–85, 86 R; 408/1 R; 433/72–76
See application file for complete search history.

(56) References Cited

U.S. PATENT DOCUMENTS

| 744,666 A | 2/1868 | Whiting | 408/202 |
|---|---|---|---|
| 2,353,514 A | 7/1944 | Slater | 408/72 |
| 2,700,905 A | 2/1955 | Urquhart | 77/55 |
| 3,000,239 A | 9/1961 | Ransom | 77/55 |
| 4,123,193 A | 10/1978 | Hill | 408/202 |
| 4,140,161 A * | 2/1979 | Russo et al. | 81/451 |
| 4,441,563 A * | 4/1984 | Walton, II | 173/213 |
| 4,710,075 A | 12/1987 | Davison | 408/202 |
| 5,078,552 A | 1/1992 | Albel | 408/1 R |
| 5,078,605 A | 1/1992 | Sutter et al. | 433/165 |
| 5,222,956 A * | 6/1993 | Waldron | 606/80 |
| 5,429,504 A | 7/1995 | Peltier et al. | 433/165 |
| 5,569,035 A | 10/1996 | Balfour et al. | 433/165 |

(Continued)

FOREIGN PATENT DOCUMENTS

| DE | 91 06 606 | 9/1992 |
|---|---|---|
| EP | 0 454 639 B1 | 3/1991 |

(Continued)

OTHER PUBLICATIONS

*3i* Implant Innovations, *Surgical Catalog*, Oct. 1996 (50 pages).

(Continued)

*Primary Examiner* — Kevin T Truong
*Assistant Examiner* — Christopher Beccia
(74) *Attorney, Agent, or Firm* — Nixon Peabody LLP

(57) ABSTRACT

A drill assembly for creating a bore in living bone comprises a drill bit, a collet-nose drill stop, a collet sleeve, a collet body, a concealment collar, a retaining spring, and a plurality of retaining balls. The drill bit inserts into the collet body and is retained in the collet body by the plurality of retaining balls. The collet-nose drill stop extends over a portion of the drill bit to limit the depth of the bore formed by the drill bit. The collet body has a drive shank and a connection region. The connection region of the collet body is adapted to receive a portion of the drill bit. The plurality of retaining balls are adapted to longitudinally secure the drill bit to the collet body.

21 Claims, 6 Drawing Sheets

U.S. PATENT DOCUMENTS

| | | | | |
|---|---|---|---|---|
| 5,575,650 | A | 11/1996 | Niznick et al. | 433/165 |
| 5,741,267 | A * | 4/1998 | Jorneus et al. | 606/102 |
| 5,785,522 | A | 7/1998 | Bergstrom et al. | 433/72 |
| 5,791,902 | A | 8/1998 | Lauks | 433/165 |
| 5,941,891 | A * | 8/1999 | Walen | 606/167 |
| 6,162,226 | A * | 12/2000 | DeCarlo et al. | 606/80 |
| 6,514,258 | B1 * | 2/2003 | Brown et al. | 606/80 |
| 6,641,395 | B2 * | 11/2003 | Kumar et al. | 433/165 |
| 6,780,189 | B2 * | 8/2004 | Tidwell et al. | 606/80 |
| 7,048,477 | B2 * | 5/2006 | Abrams | 408/1 R |
| 7,695,279 | B2 * | 4/2010 | Hirsch et al. | 433/75 |
| 7,771,143 | B2 * | 8/2010 | Bharadwaj et al. | 408/1 R |
| 7,866,979 | B2 * | 1/2011 | Verban, Jr. | 433/75 |
| 2004/0186479 | A1 * | 9/2004 | Tidwell et al. | 606/80 |
| 2006/0041268 | A1 * | 2/2006 | Shores et al. | 606/180 |
| 2006/0085005 | A1 * | 4/2006 | Kenealy et al. | 606/80 |
| 2007/0099150 | A1 * | 5/2007 | Muller et al. | 433/165 |

FOREIGN PATENT DOCUMENTS

| | | |
|---|---|---|
| EP | 0 682 917 B1 | 4/1995 |
| EP | 0 799 605 B1 | 3/1997 |
| EP | 1 386 587 A | 2/2004 |
| WO | WO 98/03119 | 1/1998 |

OTHER PUBLICATIONS

Friatec "Price List" (Oct. 1998).
Friatec "Friatec®-2, Abridged Directions for Use" (date believed to be prior to filing date of present application).
Frialit®-2, "OP-Tray Surgical Tray," set of 8 pictures (date believed to be prior to filing date of present application).
Extended Search Report for Application No. EP 08 00 0178, dated May 23, 2008 (7 pages).

* cited by examiner

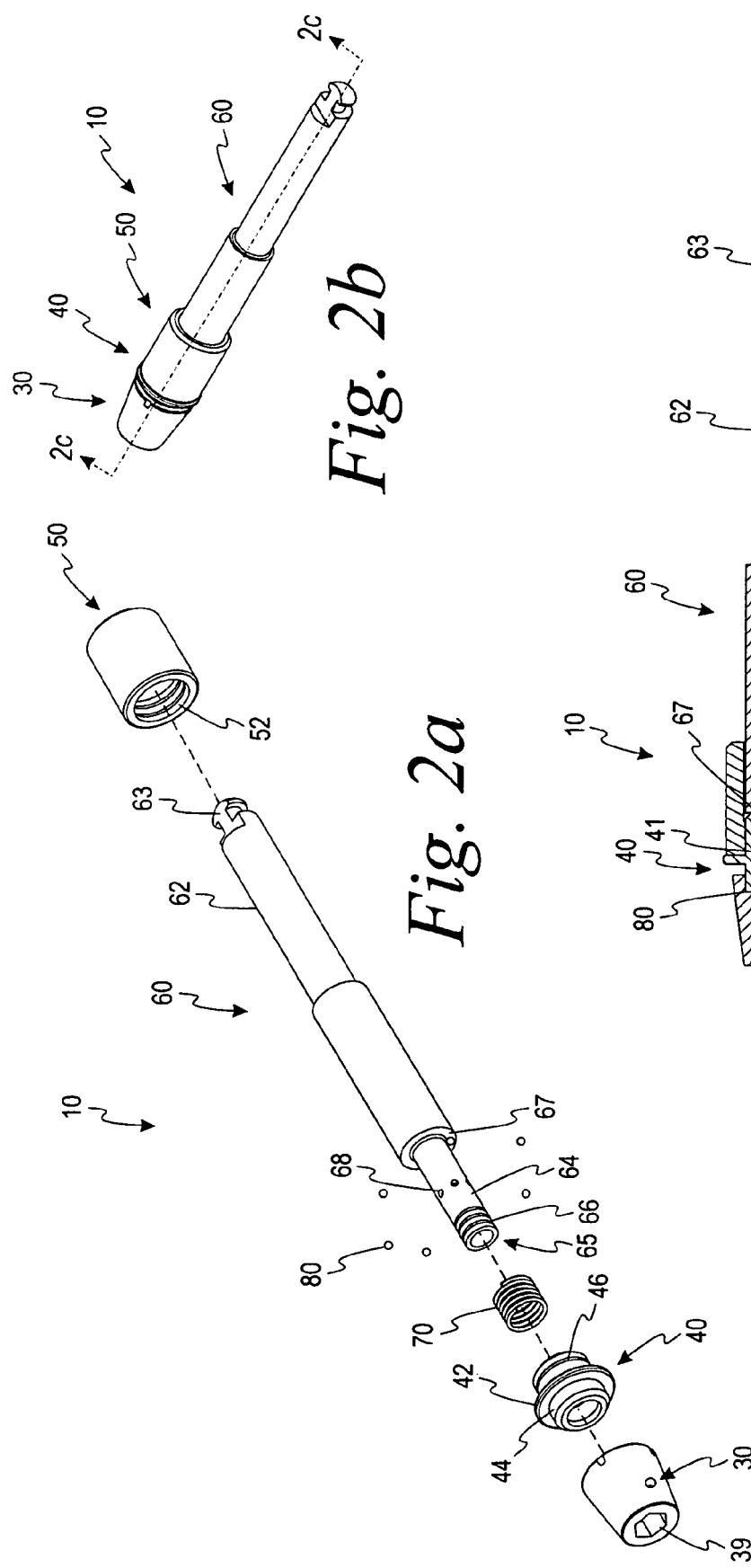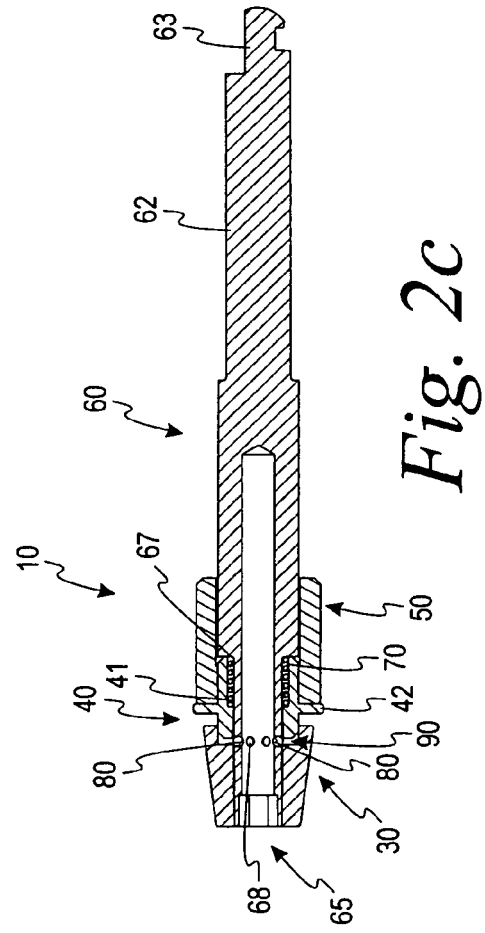

DRILL BIT ASSEMBLY FOR BONE TISSUE INCLUDING DEPTH LIMITING FEATURE

CROSS REFERENCE TO RELATED APPLICATIONS

This application claims the benefit of the U.S. Provisional Application 60/878,764, filed on Jan. 5, 2007, which is hereby incorporated by reference in its entirety.

FIELD OF INVENTION

The invention relates to devices for developing a bore in bone tissue and, in particular, to a drill bit assembly that prohibits insertion of that assembly into the bone tissue beyond a predetermined depth.

BACKGROUND OF THE INVENTION

It is common for a dentist, or oral surgeon, to use tools such as drills, to create bores in bone tissue of a patient's mouth. Drills come in various styles, sizes, and lengths, but all have a common goal of creating a bore of a known size. The diameter of the drill dictates the diameter of the bore. However, the length of the bore is determined by the amount of axial movement that the clinician imparts on the drill as he or she inserts the drill into the bone tissue.

The size of the bore is a critical parameter in the restoration of the dentition of the patient's mouth. For example, if the length of the bore is too long, it can puncture the sinus cavity if placed in the maxillary, or the mandibular canal that contains the nerves if it is placed in the mandible. Likewise, the roots of adjacent teeth also may be affected by the size of the bore.

To ensure that the drill bit is inserted into the bone to a known length, the drill bit often contains several markings on it which signify specific depths. For example, a drill bit may have a marking on it that, when located at the surface of the bone, indicates the bore depth is 10 mm. The use of these visual markers is, of course, limited to the clinician's ability to see the mark as the drill is being inserted into the patient's mouth. Accordingly, the clinician is required to keep his or her eye on the depth marker as he or she slowly proceeds with the axial movement that causes the drill bit to be inserted deeper and deeper into the bone.

Current drill bits that are adapted to be used multiple times must be sterilized between each use. However, a sterilization process may not always be properly performed, resulting in the introduction of bacteria and other pathogens to a patient. Additionally, some sterilization processes may damage certain features on a drill bit. Therefore, disposable drill bits have been utilized to eliminate the need to sterilize the drill bits, as they are only used once. A need exists for a disposable drill bit assembly with a penetration limiting stop element.

SUMMARY OF THE INVENTION

According to one embodiment, a drill assembly for creating a bore in living bone comprises a drill bit, a collet-nose drill stop, a collet sleeve, a collet body, a concealment collar, a retaining spring, and a plurality of retaining balls. The drill bit has a drive portion, an anti-rotational portion, and a plurality of flutes. The drive portion of the drill bit has a retaining groove around a periphery of the drive portion. The anti-rotational portion has a non-round cross-section. The plurality of flutes each terminate in a cutting edge adapted to create the bore in the bone. The collet-nose drill stop has a connecting ledge, an extending portion, a receptacle portion, and an anti-rotation portion. The connecting ledge contacts the drill bit to position the collet-nose drill stop relative to the drill bit. The anti-rotation portion is adapted to receive the anti-rotational portion of the drill bit. The extending portion is adapted to extend over a portion of the flutes of the drill bit to limit the depth of the bore formed by the drill bit. The collet sleeve has a protruding connection region and a first threaded region. The protruding connection region is adapted to insert into the receptacle portion of the collet-nose drill stop. The collet body has a drive shank and a connection region. The connection region of the collet body has a receiving portion, a press-fit region, a shoulder, and a plurality of retaining ball receiving holes. The receiving portion is adapted to receive the drive portion of the drill bit. The press-fit region of the collet body is adapted to connect the collet body to the collet-nose drill stop via a press-fit. The collet sleeve is adapted to be positioned over the connection region of the collet body, between the shoulder and the threaded region. The concealment collar has a threaded region adapted to connect the concealment collar to the collet sleeve via the first threaded region of the collet sleeve. The retaining spring is adapted to be positioned over the connection region of the collet body and exert a force on both the shoulder of the collet body and the collet sleeve. The plurality of retaining balls are adapted to secure the drill bit by interacting with the retaining groove of the drill bit and the plurality of retaining ball receiving holes of the collet body.

According to another embodiment, a drill assembly kit for creating a bore in living bone comprises a drill bit, a plurality of collet-nose drill stops, a collet sleeve, a collet body, a concealment collar, a retaining spring, and a plurality of retaining balls. The drill bit has a drive portion, an anti-rotational portion, and a plurality of flutes. The drive portion of the drill bit has a retaining groove around a periphery of the drive portion. The anti-rotational portion of the drill bit has a non-round cross-section. The plurality of flutes terminate in a cutting edge adapted to create the bore in the bone. The plurality of flutes further have a plurality of depth markings that indicate a distance from the cutting edge to the respective depth markings. The plurality of collet-nose drill stops each have a connecting ledge, an extending portion, a receptacle portion, and an anti-rotation portion. The connecting ledge contacts the drill bit to position the collet-nose drill stop relative to the drill bit. The anti-rotation portion being adapted to receive the anti-rotational portion of the drill bit. The extending portion is adapted to extend over a portion of the flutes of the drill bit to limit the depth of the bore formed by the drill bit. The extending portion of each of the respective collet-nose drill stops has a different length. The collet sleeve has a protruding connection region and a first threaded region. The protruding connection region is adapted to insert into the receptacle portion of the collet-nose drill stop. The collet body has a drive shank and a connection region. The connection region has a receiving portion, a press-fit region, a shoulder, and a plurality of retaining ball receiving holes. The receiving portion is adapted to receive the drive portion of the drill bit. The press-fit region of the collet body is adapted to connect the collet body to the collet-nose drill stop a press-fit. The collet sleeve is adapted to be positioned over the connection region of the collet body between the shoulder and the threaded region. The concealment collar has a threaded region adapted to connect the concealment collar to the collet sleeve via the first threaded region of the collet sleeve. The retaining spring is adapted to be positioned over the connection region of the collet body and exert a force on both the shoulder of the collet body and the collet sleeve. The plurality of retaining balls are adapted to secure the drill bit to the collet body by interacting with the retaining groove of the drill bit and the plurality of retaining ball receiving holes of the collet body.

According to a further embodiment, a drill assembly kit for creating a bore in living bone comprises a plurality of drill bits, a collet-nose drill stop, a collet sleeve, a collet body, a concealment collar, a retaining spring, and a plurality of retaining balls. The plurality of drill bits each have a drive portion, an anti-rotational portion, and a plurality of flutes. The drive portion of the drill bits have a retaining groove around a periphery of the drive portion. The anti-rotational portion of the drill bits have a non-round cross-section. The plurality of flutes terminate in a cutting edge adapted to create the bore in the bone. Each of the plurality of drill bits have a different length to create a different bore depth. The collet-nose drill stop has a connecting ledge, an extending portion, a receptacle portion, and an anti-rotation portion. The connecting ledge contacts the drill bit to position the collet-nose drill stop relative to one of the drill bits. The anti-rotation portion is adapted to receive the anti-rotational portion of the drill bit. The extending portion is adapted to extend over a portion of the flutes of one of the drill bits to limit the depth of the bore formed by the drill bit. The collet sleeve has a protruding connection region and a first threaded region. The protruding connection region is adapted to insert into the receptacle portion of the collet-nose drill stop. The collet body has a drive shank and a connection region. The connection region has a receiving portion, a press-fit region, a shoulder, and a plurality of retaining ball receiving holes. The receiving portion is adapted to receive the drive portion of the drill bit. The press-fit region of the collet body is adapted to connect the collet body to the collet-nose drill stop via a press-fit. The collet sleeve is adapted to be positioned over the connection region of the collet body between the shoulder and the threaded region. The concealment collar has a threaded region adapted to connect the concealment collar to the collet sleeve via the first threaded region of the collet sleeve. The retaining spring is adapted to be positioned over the connection region of the collet body and exert a force on both the shoulder of the collet body and the collet sleeve. The plurality of retaining balls secure the drill bit to the collet body by interacting with the retaining groove of the drill bit and the plurality of retaining ball receiving holes of the collet body.

According to yet another embodiment, a drill bit for use with a drill assembly for creating a bore in living bone comprises a drive portion, a plurality of flutes, and an anti-rotational portion. The drive portion has a retaining groove around a periphery of the drive portion. The plurality of flutes each terminate in a cutting edge adapted to create the bore in the bone. The plurality of flutes further have at least one depth marking indicating a distance from the cutting edge to the depth marking. The anti-rotational portion is located between the drive portion and the plurality of flutes. The anti-rotational portion has a non-round cross-section.

According to one process, a method of assembling a drill assembly having a drill bit, a collet-nose drill stop, a collet sleeve, a retaining spring, a collet body, a plurality of retaining balls, and a retaining spring is provided. The method locates the plurality of retaining balls within a plurality of retaining ball receiving holes of the collet body. The retaining spring positions over a connection region of the collet body. The collet sleeve is placed over the connection region of the collet body, such that the retaining spring is positioned between a shoulder of the collet body and the collet sleeve. The collet-nose drill stop attaches to the collet body, such that the collet sleeve is secured between the collet-nose drill stop and the shoulder of the collet body. The concealment collar fastens to the collet sleeve. The drill bit, that has a plurality of flutes each terminating in a cutting edge, and further has a drive portion having a retaining groove, and an anti-rotational portion, inserts into the connection region of the collet body, such that the anti-rotational portion of the drill bit interacts with an anti-rotation portion of the collet-nose drill stop. The retaining groove of the drill bit aligns with the plurality of retaining balls such that a portion of each of the retaining balls enters the retaining groove. An extending portion of the collet-nose drills top extends over a portion of the plurality of flutes of the drill bit after the drill bit is inserted into the collet body.

According to yet a further embodiment, a drill assembly for creating a bore in bone comprises a drill bit and a collet assembly. The drill bit has a drive portion, an anti-rotational portion, and a plurality of flutes that have cutting edges for creating a bore in the bone. The collet assembly has a first end and a second end. The first end includes a drive shank to couple to a drive assembly imparting motion to the collet assembly. The second end includes an opening to receive the drive portion of the drill bit and an anti-rotational feature to mate with the anti-rotational portion of the drill bit. The collet assembly includes a drill stop that fits over a portion of a length of the plurality of flutes for limiting penetration of the drill bit into the bone.

According to still yet another embodiment, a drill assembly for creating a bore in bone comprises a drill bit and a collet assembly. The drill bit has a drive portion, an anti-rotational portion, and a plurality of flutes that have cutting edges for creating a bore in the bone. The collet assembly has a first end and a second end. The first end includes a drive shank to couple to a drive assembly to impart motion to the collet assembly. The second end includes an opening to receive the drive portion of the drill bit and an anti-rotational feature to mate with the anti-rotational portion of the drill bit. The collet assembly includes a mechanism to releasably hold the drill bit within the opening.

According to still yet further embodiment, a drill assembly for creating a bore in bone comprises a drill bit, a collet assembly, and a plurality of drill stops. The drill bit has a drive portion, an anti-rotational portion, and a plurality of flutes that have cutting edges for creating a bore in the bone. The collet assembly has a first end and a second end. The first end includes a drive shank that couples to a drive assembly that imparts motion to the collet assembly. The second end includes an opening that receives the drive portion of the drill bit and an anti-rotational feature that mates with the anti-rotational portion of the drill bit. Each of the plurality of drill stops fix to the collet assembly and each have different lengths. Each of the plurality of drill stops fit over a known portion of the length of the plurality of flutes for limiting penetration of the drill bit into the bone.

BRIEF DESCRIPTION OF THE DRAWINGS

FIG. 1b is an exploded isometric view of the drill bit assembly for creating a bore bone tissue of FIG. 1a;

FIG. 1c is a cross-sectional view taken along line 1c-1c of FIG. 1a;

FIG. 2a is an exploded isometric view of the drill bit assembly of FIGS. 1a-1c with the drill bit and the extending portion of the collet-nose drill stop removed;

FIG. 2b is an isometric view of the drill bit assembly of FIGS. 1a-1c with the drill bit and the extending portion of the collet-nose drill stop removed;

FIG. 2c is a cross-sectional view taken along line 2c-2c of FIG. 2b;

Figure 1A:
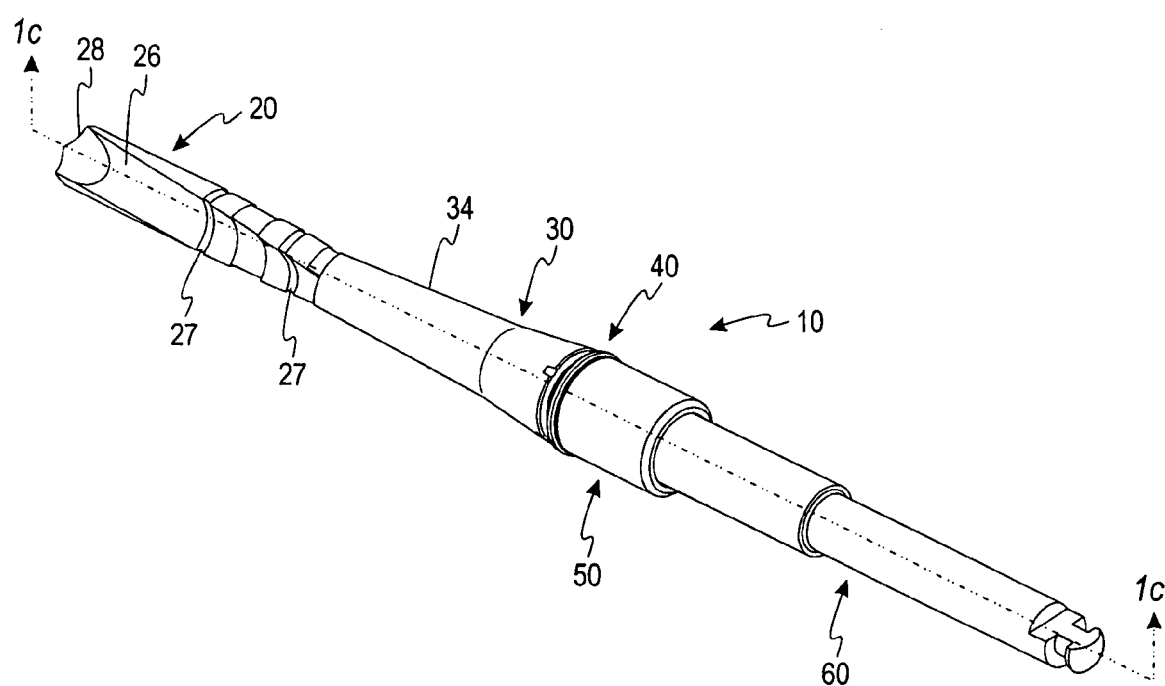
FIG. 1a is an isometric view of a drill bit assembly for creating a bore in bone tissue.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1B:
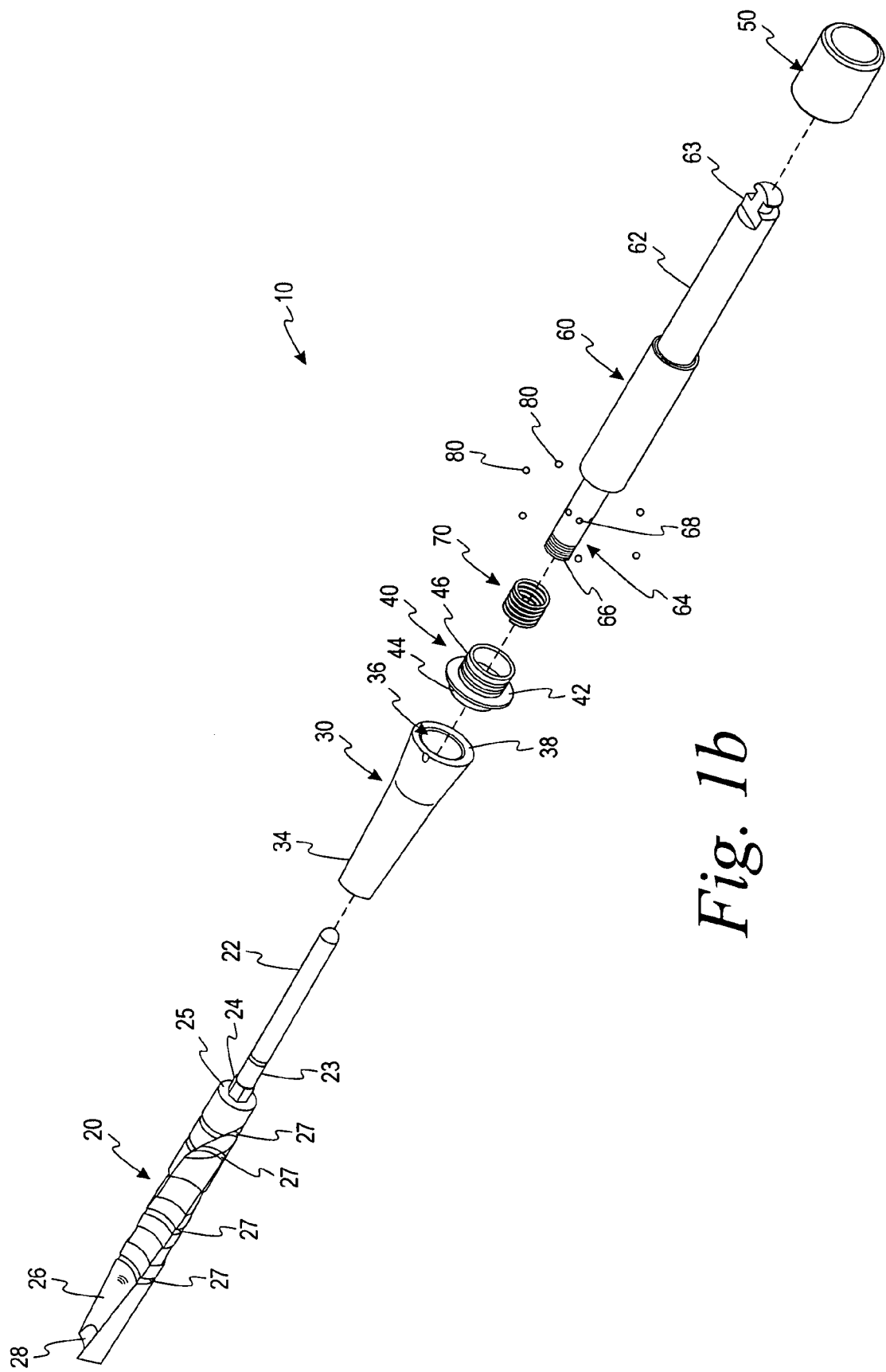
Figure 1C:
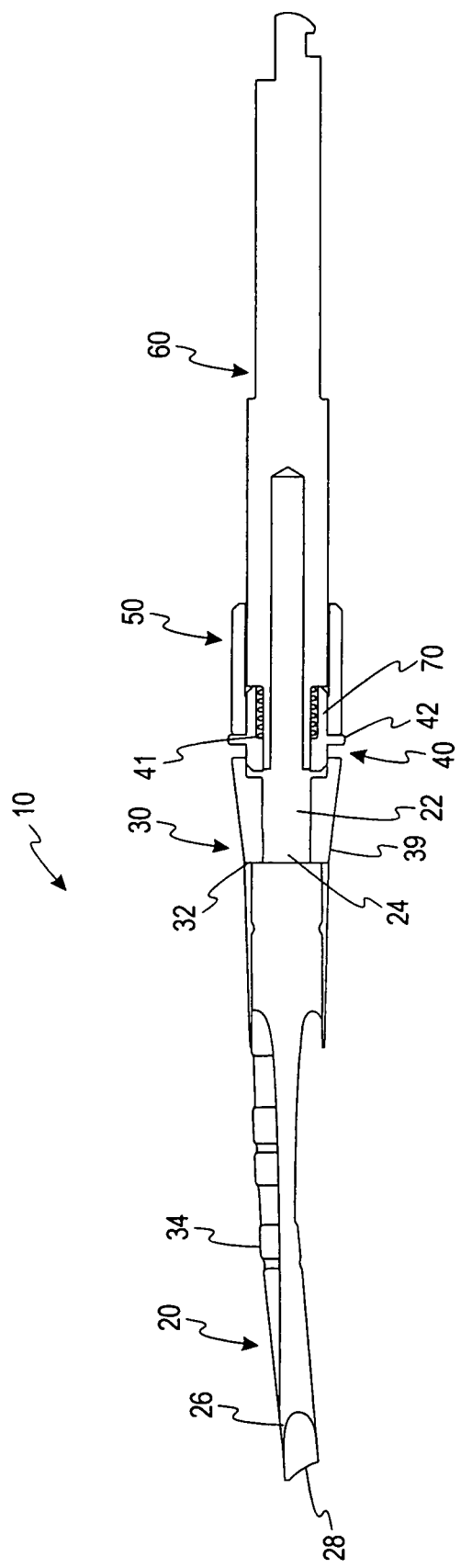

As shown in FIGS. 1a-1c, a drill assembly 10 comprises a drill bit 20, a collet nose drill stop 30, a collet sleeve 40, a concealment collar 50, a collet body 60, a retaining spring 70, and a plurality of retaining balls 80. The various components of the drill assembly 10 are each described in greater detail below.

The drill bit 20 includes a drive portion 22 at its one end that inserts into a receiving portion 65 (FIG. 2a) of the collet body 60. The drive portion 22 further has a retaining groove 23 around a periphery of the drive portion 22. The retaining groove 23 receives the plurality of retaining balls 80 to secure the drill bit 20 within the drill assembly 10. An anti-rotational portion 24 is located at a shoulder 25. The anti-rotational portion 24 shown in FIGS. 1a-1c has a hexagonal shape, but any other non-round cross sectional shape may be utilized. Each of a plurality of flutes 26 terminates in a cutting edge 28 which slices the bone tissue to develop a bore. The flutes 26 may further have a plurality of depth makings 27. Each marking 27 signifies a known distance from the cutting edges 28. The drill bit 20 is typically made of stainless steel, although other materials may be used. The drill bit 20 may be sterilized, such as being placed in an autoclave, for reuse, or the drill bit 20 may be disposable and only used on a single patient.

The collet-nose drill stop 30 positions over a portion of the drill bit 20 such that an extending portion 34 of the collet-nose drill stop 30 extends over the flutes 26 of the drill bit 20. The collet-nose drill stop 30 includes a connecting ledge 32 contacts the shoulder portion 25 of the drill bit 20. The connecting ledge 32 rests on the shoulder 25 of the drill bit 20 to properly position the collet-nose drill stop 30. The extending portion 34 extends over the a portion of the flutes 26 of the drill bit 20 to limit the depth of the bore formed by the drill bit 20, such that the drill stop 30 may limit the depth of the bore made by the drill bit 20 to the desired depth. The length of the extending portion 34 of the drill stop 30 determines the depth of the bore formed by the drill bit 20 of the drill assembly 10. For example, a longer extending portion 34 will result in a shallower bore being formed, as a lesser amount of the flutes 26 of the drill bit 20 are exposed. Similarly, a shorter extending portion 34 results in a deeper bore being formed as a greater amount of the flutes 26 of the drill bit 20 are exposed.

The drill stop 30 further has a receptacle portion 36 that interacts with a protruding portion 44 of the collet sleeve 40 to properly position the collet-nose drill stop 30 relative to the collet sleeve 40. The receptacle portion 36 of the drill stop 30 terminates at a collet-nose drill-stop shoulder 38. The collet-nose drill stop 30 further has an anti-rotation portion 39 located on an opposite side of the shoulder 38 as the receptacle portion 36. The anti-rotation portion 39 has a complimentary shape to the anti-rotational portion 24 of the drill bit 20. The collet-nose drill stop 30 is press-fit to the collet body 60. It is contemplated according to an alternative embodiment that a collet-nose drill stop may connect to a collet body via threads or other fastening methods.

The collet sleeve 40 allows the drill bit 20 to be secured within the drill bit assembly 10. The collet sleeve 40 has an internal ledge 41 and an external shoulder portion 42. The internal ledge 41 secures the retaining spring 70 of the drill assembly 10. The external shoulder portion 42 separates a protruding connection region 44 from a first threaded region 46. The protruding connection region 44 inserts into the receptacle portion 36 of the collet nose drill stop 30. The insertion of the protruding connection region 44 of the collet sleeve 40 positions the plurality of retaining balls 80 so as to secure the drill bit 20, as described below in greater detail. The first threaded region 46 interacts with a threaded region 52 (FIG. 2a) of the concealment collar 50 to connect the collet sleeve 40 to the concealment collar 50.

Still referring to FIGS. 1a-1c, the collet body 60 has a drive shank 62 at its one end that terminates in a drive attachment 63. The drive attachment 63 is configured to mate with a corresponding dental drill handpiece, or like device, that imparts rotating motion to the collet body 60 and the drill assembly 10. One common drive attachment is an ISO-latch, as shown in FIGS. 1a-1c. The collet body 60 has a connection region 64 at its other end that allows assembly of the drill assembly 10. The connection region 64 has a receiving portion 65 (FIGS. 2a, 2c) to receive the drive portion 22 of the drill bit 20. The connection region 64 further has press-fit region 66 to connect the collet body 60 to the collet-nose drill stop 30. Additionally, the connection region 64 of the collet body 60 has a shoulder 67 (FIG. 2a) for engaging the retaining spring 70 between the shoulder 67 of the collet body 60 and the internal ledge 42 of the collet sleeve 40. The connection region 64 further has a plurality of receiving holes 68 to receive the retaining balls 80. It is contemplated according to an alternative embodiment that the press-fit region 66 may be replaced with a threaded region to connect a collet-nose drill stop to a collet body.

To assemble the pieces of the drill assembly 10, the retaining spring 70 slides over the connection region 64 of the of the collet body 60 to the shoulder 67. The plurality, of retaining balls 80 are then inserted into each of the respective plurality of receiving holes 68 of the collet body. Next, the collet sleeve 40 slides over the connection region 64 of the collet body 60. The internal ledge 41 of the collet sleeve 40 contacts the retaining spring 70. Once the collet sleeve 40 is in position, the concealment collar 50 slides over the drive portion 62 of the collet body 60. The first threaded region 46 of the collet sleeve 40 threads into the threaded region 52 of the concealment collar 50. The connection of the collet sleeve 40 and the concealment collar 50 secure the retaining spring 70 between the shoulder 67 of the collet body 60 and the internal ledge 41 of the collet sleeve 40. The retaining spring 70 thus exerts a force against both the shoulder 67 and the internal ledge 41 to bias the collet sleeve 40 towards the connection region 64 of the collet body 60. The collet-nose drill stop 30 is then slid onto the connection region 64 of the collet body 60 and the receptacle portion 36 of the collet-nose drill stop 30 receives the protruding portion 44 of the collet sleeve 40. The collet-nose drill stop 30 then is secured via a press-fit to the collet body 60.

To insert the drill bit 20 into the assembly 10, the concealment collar 50 is pulled towards the drive shank 62 of the collet body 60, thus compressing the retaining spring 70 as the collet sleeve 40 moves with the concealment collar 50. The movement of the collet sleeve 40 creates a gap 90 (FIG. 2c) allowing the retaining balls 80 to be displaced. The drive portion 22 of the drill bit 20 is then inserted into the receiving portion 65 of the connection region until the anti-rotational portion 24 of the drill bit 20 is within the anti-rotation portion 39 of the collet-nose drill stop body 30. As the drive portion 22 is inserted into the collet body 60, the retaining balls 80 are displaced by the drive portion 22 until the retaining groove 23 is aligned with the retaining ball receiving holes 68. After the drive portion of the drill bit 20 is inserted into the collet body 60, the concealment collar 50 may be released and the retaining spring 70 presses against the collet sleeve 40 to move the collet sleeve 40 from an installation position to an operational position. Once the retaining groove 23 is aligned with the retaining ball receiving holes 68, the retaining balls 80 engage the retaining groove 23 of the drill bit 20. The biasing force of the retaining spring 70 on the collet sleeve 40 causes the collet sleeve 40 to move away from the drive shank 62 of the collet body 60, causing the collet sleeve 40 to press on the retaining balls 80 so that they engage the retaining groove 23 of the drill bit 20. The engagement of the retaining groove 23 by the retaining balls 80 prevent the drill bit 20 from moving in an axial direction relative to the collet body 60. The drill assembly 10 is then ready to be inserted into a drill handpiece.

Turning now to FIGS. 2a-2c, the drill assembly 10 is shown without the drill bit 20 and without the extending portion 34 of the collet-nose drill stop 30 to allow for greater clarity of the other components. As can best be viewed in FIG. 2c, a gap 90 exists between the collet-nose drill stop shoulder 38 and an end of the protruding connection region 44 of the collet sleeve 40. As the concealment collar 50 is pulled back towards the drive shank 62, the gap 90 forms as the collet sleeve 40 moves away from the collet-nose drill stop 30, and the plurality of retaining balls 80 may be displaced into the gap 90. As the concealment collar 50 is returned to its operational position, the gap 90 decreases and the plurality of retaining balls 80 are forced into the retaining ball receiving holes 68 so that the retaining balls 80 may engage a drill bit.

Figure 3:
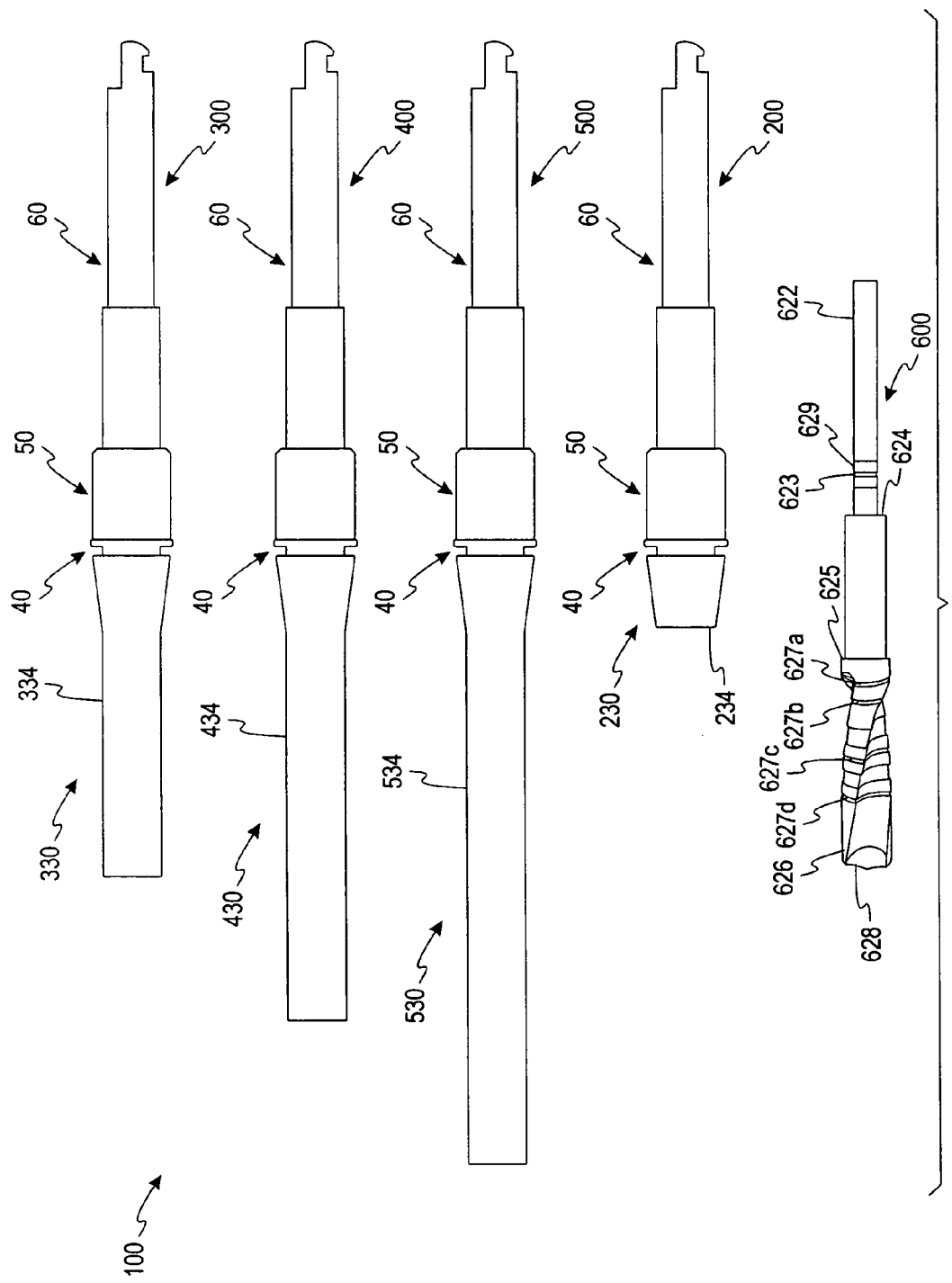
FIG. 3 is a side view of a drill assembly kit according to one embodiment.

Turning now to FIG. 3 a drill assembly kit 100 is shown that comprises a first drill assembly 200, a second drill assembly 300, a third drill assembly 400, and a fourth drill assembly 500. The drill assemblies 200-500 that make up the kit 100 are similar to the drill assembly 10 previously described, except that different collet-nose drill stops 230, 330, 430, and 530 are utilized.

FIG. 3 also illustrates a drill bit 620 that is similar to drill bit 20, and includes similar features shown in the 600-series reference numerals. A drive portion 622 is located at its one end and has a retaining groove 623 around a periphery of the drive portion 622. The retaining groove 623 receives the plurality of retaining balls as previously described in connection with FIGS. 1a-1c to secure the drill bit 620 to the drill assembly. The drive portion 622 transitions via an anti-rotational portion 624 located at a shoulder 625 to a plurality of flutes 626. The anti-rotational portion 624 has a non-round cross-sectional shape. Each of the flutes 626 terminates in a cutting edge 628 which slices the bone tissue to develop a bore. The flutes 626 further have a plurality of depth makings 627a-d. Each marking 627a-d signifies a known distance from the cutting edges 628. The retaining groove 623 is used to secure the drill bit to the drill assemblies 300-500 as previously described.

Unlike the drill bit 20, the drill bit 620 has a deformable area 629 surrounding the retaining groove 623. The deformable area 629 deforms if the drill bit 600 is sterilized via a heating process, such as being sterilized in an autoclave, such that the retaining groove 623 will no longer function to retain the drill bit 600 within a drill assembly. It is contemplated that the deformable area 629 would be made of a polymeric material that loses its shape when exposed to high heat levels. Using a deformable area 629 on the drill bit 620 reduces the risk of infection that may result, as the drill bit 620 may not be used on multiple patients. The drill bit 620 is thus, disposable, in that it is intended to only be used on one patient.

The collet-nose drill stops 230-530 are similar to the collet-nose drill stop 30 previously described, except the length of extending portions 234-534 vary on the respective collet-nose drill stops 230-530 of the kit 100. The collet-nose drill stop 230 has the shortest extending portion 234 of the kit 100, and the extending portion 234 may only extend to the marking 627a of the drill bit 600. The collet-nose drill stop 330 is the next shortest of the kit 100, with an extending portion 334 reaching to the depth marking 627b of the drill bit 600. The collet-nose drill stop 430 has the next greatest length of the collet-nose drill stops of the kit 100, wherein the extending portion 434 extends to the depth marking 627c of the drill bit 620. Finally, the collet-nose drill stop 530 has the longest extending portion 534 that extends to the depth marking 627d of the drill bit 620. Thus, the longest bore may be formed by the use of drill assembly 200, while the shortest bore is made with drill assembly 500.

It is contemplated that the components of the drill assembly kit 100, other than the disposable drill bit 620, are reusable in that the components may be sterilized, such as in an autoclave, and used on multiple patients.

Providing a drill assembly kit 100 as shown in FIG. 3 allows a clinician to have available a number of collet-nose drill stops 230-530 of various lengths, such that a collet-nose drill stop may be selected to be used to form a bore of a desired depth. It is also contemplated that additional drill bits of various diameters may also be provided in the drill assembly kit 100, to allow for different diameter bores to be formed.

Figure 4:
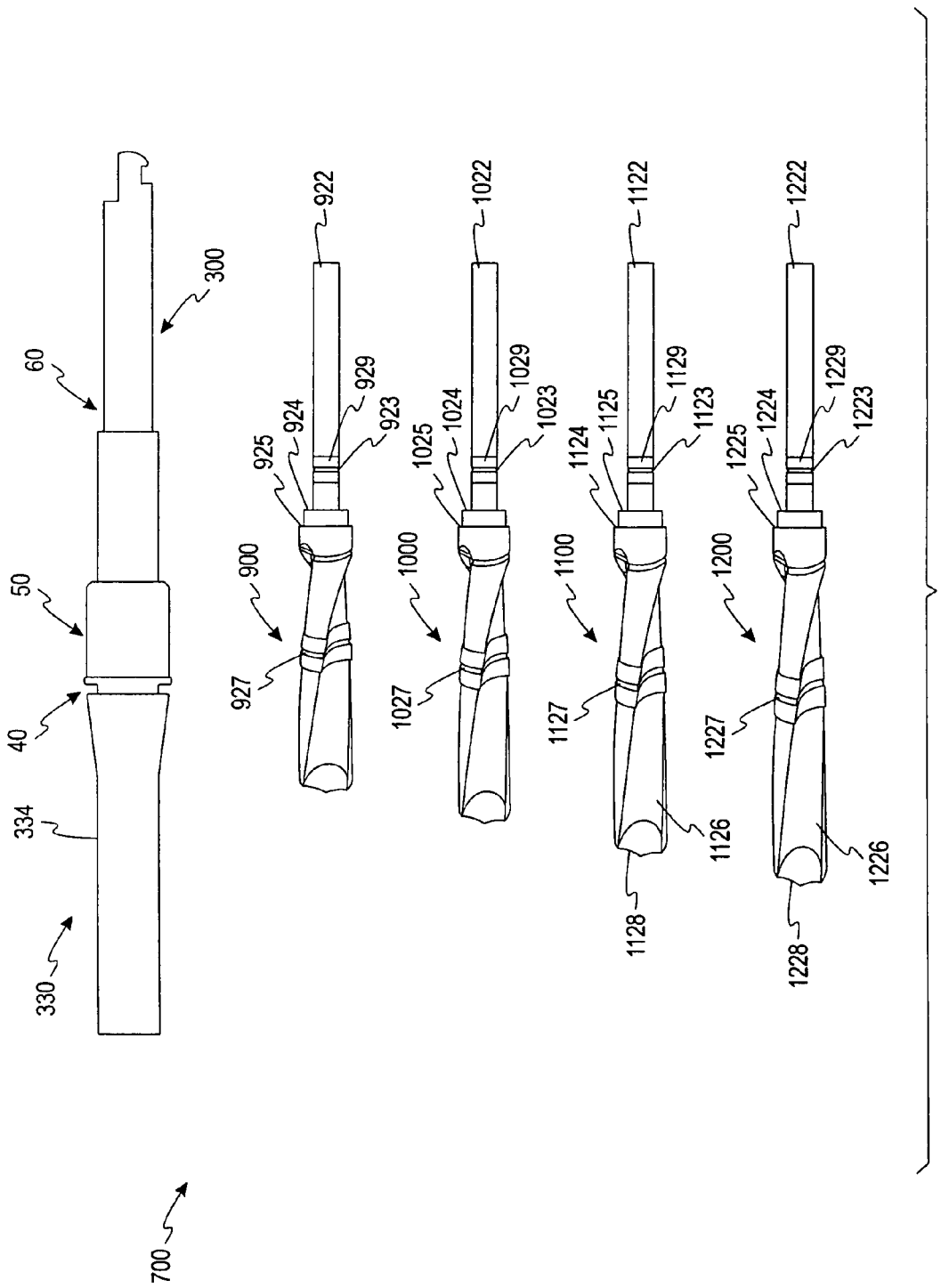
FIG. 4 is a side view of a drill assembly kit according to another embodiment.

Next, as shown in FIG. 4 a drill assembly kit 700 comprises a drill assembly 800 and drill bits 900-1200 to be used with the drill assembly 800. The drill assembly 800 that make up the drill assembly kit 700 is similar to the drill assembly 10 previously described, except that a different collet-nose drill stop 830 is utilized. A plurality of drill bits 900-1200 are utilized with the drill assembly 800.

The collet-nose drill stop 830 is similar to the collet-nose drill stop 30 previously described, except the length of an extending portion 834 on the collet-nose drill stop 830 of the kit 700 may be different than that of the previously described collet-nose drill stop 30. The extending portion 834 of the collet-nose drill stop 830 extends to a depth marking 927, 1027, 1127, 1227 of the respective drill bit 920, 1020, 1120, 1220 when the respective drill bits are used in the drill assembly 800.

As shown in FIG. 4, the drill bit 920 has a smaller diameter than the drill bits 1020, 1120, and 1220. The drill bit 920 may be used to drill a pilot bore prior to using one of the other drill bits 1020, 1120, 1220 of the kit 700.

The drill bit 920 shown includes a drive portion 922 at its one end that further has a retaining groove 923 around a periphery of the drive portion 922. The retaining groove 923 receives the plurality of retaining balls as previously described in connection with FIGS. 1a-1c to secure the drill bit 920 to the drill assembly. The drive portion 922 transitions via an anti-rotational portion 924 located at a shoulder 925 to a plurality of flutes 926. The anti-rotational portion 924 has a non-round cross sectional shape. Each of the flutes 926 terminates in a cutting edge 928 which slices the bone tissue to develop a bore. The flutes 926 further has a depth making 927. The marking 927 signifies a known distance from the cutting edges 928. The retaining groove 923 is used to secure the drill bit to the drill assemblies 800 as previously described in connection with FIGS. 1 and 2. The drill bit 920 is the shortest drill bit of the kit 700.

The drill bits 1020, 1120, 1220 have similar features to the drill bit 920, except they are represented by 1000-series, 1100-series, and 1200-series reference numerals respectively. The drill bit 1020 is the second shortest drill bit of the kit 700. The drill bit 1120 is the second longest drill bit of the kit 700. The drill bit 1220 is the longest of the kit 700.

As shown in FIG. 4, the length of each of the drill bits 920, 1020, 1120, 1220 vary, but the distance from the retaining groove 923, 1023, 1123, 1223 to the shoulder 925, 1025, 1125, 1225 of each of the drill bits 900, 1000, 1100, 1200 is generally identical.

It is additionally contemplated that the drill bits 920, 1020, 1120, 1220 may additional have a deformable area surrounding the retaining groove 923, 1023, 1123, 1223, such as that described in connection with drill bit 620 of FIG. 3. The deformable areas 923, 1023, 1123, 1223 deform if a drill bit is placed is sterilized in a heating process, such as in an autoclave, such that the retaining groove will no longer function to retain the drill bit within a drill assembly. Thus, the drill bits 920, 1020, 1120, 1220 may be disposable, in that they are intended to only be used on one patient when they contain the deformable area 923, 1023, 1123, 1223.

It is contemplated that the components of the drill assembly kit 700, other than drill bits 920, 1020, 1120, and 1220, are reusable in that the components may be sterilized, such as in an autoclave, and used on multiple patients. However, if drill bits provided do not have a deformable area, drill bits may also be sterilized and used on multiple patients.

Providing a drill assembly kit 700 as shown in FIG. 4 allows a clinician to have available a number of drill bits 920-1220 of various lengths, such that a drill bit may be selected to be used with the drill assembly 800 to form a bore of a desired depth. It is also contemplated that additional drill bits of various diameters may also be provided in the drill assembly kit 700, to allow for additional different diameter bores to be formed.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A drill assembly for creating a bore in bone comprising:
   a drill bit having a drive portion, an anti-rotational portion, and a plurality of flutes having cutting edges for creating a bore in the bone; and
   a collet assembly having a first end and a second end, the first end including a drive shank for being coupled to a drive assembly imparting motion to the collet assembly, the second end including an opening for receiving the drive portion of the drill bit and an anti-rotational feature for mating with the anti-rotational portion of the drill bit such that motion imparted to the collet assembly via the drive shank is thereby imparted to the drill bit via the drive portion, the collet assembly including a drill stop for fitting over a portion of a length of the plurality of flutes for limiting penetration of the drill bit into the bone.

2. The drill assembly of claim 1, wherein the collet assembly includes a component within the opening for releasably engaging the drive portion of the drill bit.

3. The drill assembly of claim 2, wherein the component is a plurality of retaining balls that engage a groove within the drive portion of the drill bit.

4. The drill assembly of claim 3, wherein the collet assembly includes a retractable portion for allowing the balls to move into and out of the plurality of grooves during the releasable engagement.

5. The drill assembly of claim 4, wherein the assembly includes a spring adapted to bias the retractable portion to an operating position.

6. The drill assembly of claim 4, wherein the assembly includes a grip portion for grasping the retractable portion.

7. The drill assembly of claim 1, wherein the drive shank is an ISO-latch connector.

8. The drill assembly of claim 1, wherein the drive portion of the drill bit has a deformable area including a groove.

9. The drill assembly of claim 8, wherein the drill bit is disposable.

10. A drill assembly for creating a bore in bone comprising:
    a drill bit having a drive portion, an anti-rotational portion, and a plurality of flutes having cutting edges for creating a bore in the bone; and
    a collet assembly having a first end and a second end, the first end including a drive shank for being coupled to a drive assembly imparting motion to the collet assembly, the second end including an opening for receiving the drive portion of the drill bit and an anti-rotational feature for mating with the anti-rotational portion of the drill bit, the collet assembly including a mechanism for releasably holding the drill bit within the opening such that motion imparted to the collet assembly via the drive shank is thereby imparted to the drill bit via the drive portion.

11. The drill assembly of claim 10, wherein the mechanism for releasably holding the drill bit includes a plurality of retaining balls that engage a groove within the drive portion of the drill bit.

12. The drill assembly of claim 11, wherein the collet assembly includes a retractable portion for allowing the balls to move into and out of the plurality of grooves during the releasable engagement.

13. The drill assembly of claim 10, wherein the drive portion of the drill bit has a deformable area including a groove.

14. The drill assembly of claim 13, wherein the drill bit is disposable.

15. The drill assembly of claim 10, wherein the collet assembly further includes a drill stop for fitting over a portion of a length of the plurality of flutes of the drill bit for limiting penetration of the drill bit into bone.

16. A drill assembly for creating a bore in bone comprising:
    a drill bit having a drive portion, an anti-rotational portion, and a plurality of flutes having cutting edges for creating a bore in the bone; and
    a collet assembly having a first end and a second end, the first end including a drive shank for being coupled to a drive assembly imparting motion to the collet assembly, the second end including an opening for receiving the drive portion of the drill bit and an anti-rotational feature for mating with the anti-rotational portion of the drill bit such that motion imparted to the collet assembly via the drive shank is thereby imparted to the drill bit via the drive portion; and a plurality of drill stops, each of the plurality of drill stops for being fixed to the collet assembly and each having different lengths, each of the plurality of drill stops fitting over a known portion of the length of the plurality of flutes for limiting penetration of the drill bit into the bone.

17. The drill assembly of claim 16, wherein the drill bit has a plurality of depth markings on the plurality of flutes indicating a distance from the cutting edges to the depth marking.

18. The drill assembly of claim 17, wherein at least one of the plurality of drill stops fits over a portion of the plurality of flutes to at least one of the plurality of depth markings.

19. A drill assembly kit for creating a bore in living bone comprising:
- a plurality of drill bits, each of the plurality of drill bits having a drive portion, an anti-rotational portion, and a plurality of flutes, the drive portion of the drill bit having a retaining groove around a periphery of the drive portion, the anti-rotational portion having a non-round cross-section, the plurality of flutes terminating in a cutting edge adapted to create the bore in the bone, each of the plurality of drill bits having a different length to create a different bore depth;
- a collet-nose drill stop having a connecting ledge, an extending portion, a receptacle portion, and an anti-rotation portion, the connecting ledge contact the drill bit to position the collet-nose drill stop relative to the drill bit, the anti-rotation portion being adapted to receive the anti-rotational portion of the drill bit, the extending portion being adapted to extend over a portion of the flutes of the drill bit to limit the depth of the bore formed by the drill bit;
- a collet sleeve having a protruding connection region and a first threaded region, the protruding connection region being adapted to insert into the receptacle portion of the collet-nose drill stop;
- a collet body having a drive shank and a connection region, the connection region having a receiving portion, a press-fit region, a shoulder, and a plurality of retaining ball receiving holes, the receiving portion being adapted to receive the drive portion of the drill bit, the press-fit region of the collet body being adapted to connect the collet body to the collet-nose drill stop via a press-fit, the collet sleeve being adapted to be positioned over the connection region of the collet body between the shoulder and the threaded region;
- a concealment collar having a threaded region adapted to connect the concealment collar to the collet sleeve via the first threaded region of the collet sleeve;
- a retaining spring adapted to be positioned over the connection region of the collet body and exert a force on the shoulder of the collet body and the collet sleeve; and
- a plurality of retaining balls adapted to secure the drill bit by interacting with the retaining groove of the drill bit and the plurality of retaining ball receiving holes of the collet body.

20. A drill assembly kit for creating a bore in living bone comprising:
- a drill bit having a drive portion, an anti-rotational portion, and a plurality of flutes, the drive portion of the drill bit having a retaining groove around a periphery of the drive portion, the anti-rotational portion having a non-round cross-section, the plurality of flutes terminating in a cutting edge adapted to create the bore in the bone, the plurality of flutes further having a plurality of depth markings indicating a distance from the cutting edge to the depth marking;
- a plurality of collet-nose drill stops, each of the drill stops having a connecting ledge, an extending portion, a receptacle portion, and an anti-rotation portion, the connecting ledge contact the drill bit to position the collet-nose drill stop relative to the drill bit, the anti-rotation portion being adapted to receive the anti-rotational portion of the drill bit, the extending portion being adapted to extend over a portion of the flutes of the drill bit to limit the depth of the bore formed by the drill bit, the extending portion of each of the respective collet-nose drill stops having a different length;
- a collet sleeve having a protruding connection region and a first threaded region, the protruding connection region being adapted to insert into the receptacle portion of the collet-nose drill stop;
- a collet body having a drive shank and a connection region, the connection region having a receiving portion, a press-fit region, a shoulder, and a plurality of retaining ball receiving holes, the receiving portion being adapted to receive the drive portion of the drill bit, the press-fit region of the collet body being adapted to connect the collet body to the collet-nose drill stop via a press-fit, the collet sleeve being adapted to be positioned over the connection region of the collet body between the shoulder and the threaded region;
- a concealment collar having a threaded region adapted to connect the concealment collar to the collet sleeve via the first threaded region of the collet sleeve;
- a retaining spring adapted to be positioned over the connection region of the collet body and exert a force on the shoulder of the collet body and the collet sleeve; and
- a plurality of retaining balls adapted to secure the drill bit by interacting with the retaining groove of the drill bit and the plurality of retaining ball receiving holes of the collet body.

21. A drill assembly for creating a bore in living bone comprising:
- a drill bit having a drive portion, an anti-rotational portion, and a plurality of flutes, the drive portion of the drill bit having a retaining groove around a periphery of the drive portion, the anti-rotational portion having a non-round cross-section, the plurality of flutes each having a cutting edge adapted to create the bore in the bone;
- a collet-nose drill stop having a connecting ledge, an extending portion, a receptacle portion, and an anti-rotation portion, the connecting ledge contacting the drill bit to position the collet-nose drill stop relative to the drill bit, the anti-rotation portion being adapted to receive the anti-rotational portion of the drill bit, the extending portion being adapted to extend over a portion of the flutes of the drill bit to limit the depth of the bore formed by the drill bit;
- a collet sleeve having a protruding connection region and a first threaded region, the protruding connection region adapted for inserting into the receptacle portion of the collet-nose drill stop;
- a collet body having a drive shank and a connection region, the connection region having a receiving portion, a press-fit region, and a plurality of receiving holes, the receiving portion being adapted to receive the drive portion of the drill bit, the press-fit region of the collet body being adapted to connect the collet body to the collet-nose drill stop via a press-fit, the collet sleeve being adapted to be positioned over the connection region of the collet body;

a concealment collar having a threaded region adapted to connect the concealment collar to the collet sleeve via the first threaded region of the collet sleeve; and a plurality of retaining balls adapted to secure the drill bit by interacting with the retaining groove of the drill bit and the plurality of retaining ball receiving holes of the collet body.

* * * * *